(12) United States Patent
Wang et al.

(10) Patent No.: US 9,012,468 B2
(45) Date of Patent: Apr. 21, 2015

(54) ONE POT PROCESS FOR PRODUCING 6-HYDROXYL NAL-OPIATE

(71) Applicant: Mallinckrodt LLC, Hazelwood, MO (US)

(72) Inventors: Peter X. Wang, Creve Coeur, MO (US); Tao Jiang, Chesterfield, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 13/762,431

(22) Filed: Feb. 8, 2013

(65) Prior Publication Data

US 2013/0203999 A1    Aug. 8, 2013

Related U.S. Application Data

(60) Provisional application No. 61/596,256, filed on Feb. 8, 2012.

(51) Int. Cl.

| | | |
|---|---|---|
| C07D 221/22 | (2006.01) | |
| C07D 271/00 | (2006.01) | |
| C07D 491/00 | (2006.01) | |
| C07D 498/00 | (2006.01) | |
| C07D 513/00 | (2006.01) | |
| C07D 515/00 | (2006.01) | |
| C07D 489/00 | (2006.01) | |
| A01N 43/42 | (2006.01) | |
| A61K 31/42 | (2006.01) | |
| C07D 489/08 | (2006.01) | |
| C07D 489/02 | (2006.01) | |

(52) U.S. Cl.
CPC ............ *C07D 489/08* (2013.01); *C07D 489/02* (2013.01)

(58) Field of Classification Search
USPC .......................................................... 546/44
See application file for complete search history.

(56) References Cited

U.S. PATENT DOCUMENTS

| | | | |
|---|---|---|---|
| 7,985,858 B2 | 7/2011 | Grote et al. | |
| 8,101,757 B2 | 1/2012 | Wang et al. | |
| 8,148,528 B2 | 4/2012 | Wang et al. | |
| 8,217,175 B2 | 7/2012 | Wang et al. | |
| 8,273,888 B2 | 9/2012 | Grote et al. | |
| 8,309,727 B2 | 11/2012 | Wang et al. | |
| 2009/0312552 A1* | 12/2009 | Bao et al. | ......................... 546/44 |

FOREIGN PATENT DOCUMENTS

| | | |
|---|---|---|
| WO | 2008118654 A1 | 10/2008 |
| WO | 2008130553 A1 | 10/2008 |
| WO | 2008137672 A1 | 11/2008 |
| WO | WO 2009092912 * | 7/2009 |
| WO | 2011/021029 A1 | 2/2011 |

OTHER PUBLICATIONS

De Vries; J. Org. Chem.(1980),45,4126-4129.*
Anderson; Practical Process Research and Development, 2000, Academic Press, p. 34.*
Chatterjie et al. "Stereospecific synthesis of the 6.beta.-hydroxy metabolites of naltrexone and naloxone"; Journal of Medicinal Chemistry, 1975, pp. 490-492 18 (5).

* cited by examiner

*Primary Examiner* — John Mabry
*Assistant Examiner* — Daniel Carcanague

(57) ABSTRACT

The present invention provides processes for preparing nal-opiates without the isolation of intermediates. In general, the process provides for alkylation and reduction in the same pot to give the nal-opiate.

20 Claims, No Drawings

ONE POT PROCESS FOR PRODUCING 6-HYDROXYL NAL-OPIATE

CROSS REFERENCE TO RELATED APPLICATIONS

This application claims the benefit of U.S. Provisional Application No. 61/596,256 filed Feb. 8, 2012, which is incorporated herein in its entirety.

FIELD OF THE INVENTION

The present invention relates to improved processes for preparing nal-opiates. The processes generally avoid the isolation of intermediate structures in the multi-step synthesis.

BACKGROUND OF THE INVENTION

Opiate alkaloids are important pharmaceuticals for a variety of purposes. "Nal"-opiates are a class of alkaloids containing tertiary amines which includes, among others, α- or β-naloxol. Nal-opiates share a basic morphinan chemical structure and include a tertiary amine at the N-17 position. They are particularly useful as competitive antagonists of opioid compounds, and as such are widely used in treating substance abuse and addiction.

Production of nal-opiates generally proceeds through a number of synthetic steps, where each step requires isolation of the intermediate before the next synthetic step can be performed. Isolation becomes necessary for a number of reasons, including because byproducts of the reaction interfere with later synthetic steps which may lower the yield or halt the reaction altogether. Moreover, isolation of intermediates itself is an extra synthetic step that can lower the yield and efficiency of the total synthesis. For example, some syntheses require that intermediates be purified through a number of steps so that the remainder of the reaction can proceed in high yield.

Thus, there is a need for routes to nal-opiates which do not require the isolation of intermediates.

SUMMARY OF THE INVENTION

The present invention relates to an improved process for preparing opiate alkaloids without the isolation of intermediates.

In one aspect, the disclosure provides a one pot process for preparing a 6-hydroxyl nal-opiate from a 6-keto nor-opiate. The process comprises (a) contacting the 6-keto nor-opiate with an alkylating reagent to form a 6-keto nal-opiate, wherein the 6-keto nal-opiate is not isolated; and (b) contacting the 6-keto nal-opiate with a reducing agent and a proton acceptor to form the 6-hydroxyl nal-opiate.

In another aspect, the present disclosure provides a one pot process for producing a compound comprising Formula (I) from a compound comprising Formula (II). The process comprises (a) contacting the compound comprising Formula (II) with an alkylating reagent comprising $R^{17}$ to form an intermediate comprising Formula (III), wherein the intermediate comprising Formula (III) is not isolated; and (b) contacting the intermediate comprising Formula (III) with a reducing agent and a proton acceptor to form the compound comprising Formula (I) according to the reaction scheme:

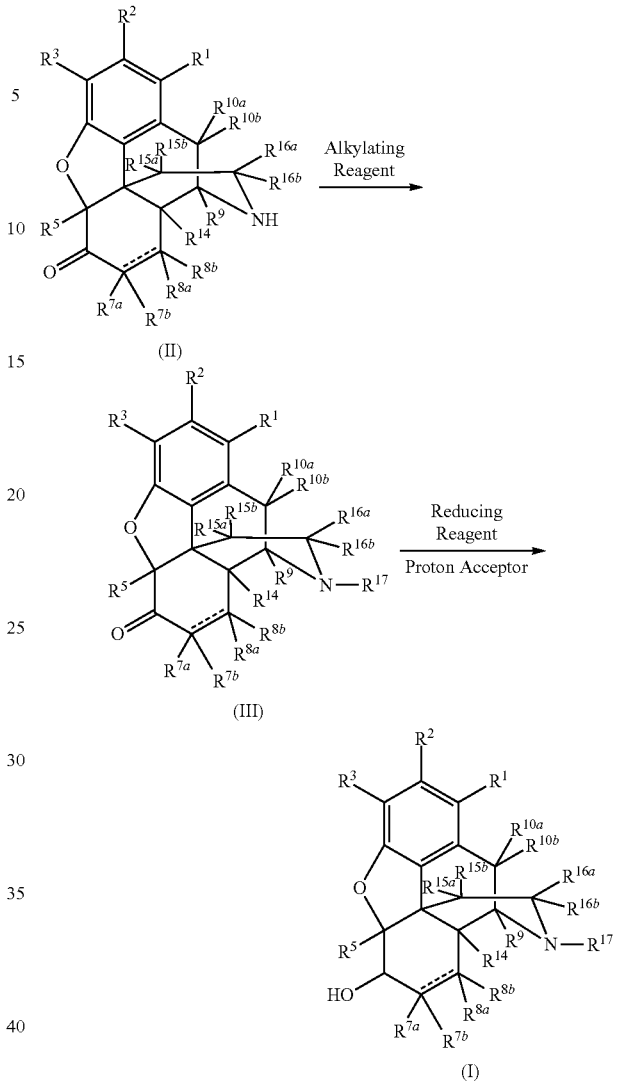

wherein, $R^1$, $R^2$, and $R^3$ are independently chosen from hydrogen, hydrocarbyl, substituted hydrocarbyl, halogen, hydroxyl, SH, $SR^{1811}$, $OR^{1811}$, and $NR^{1811}R^{1812}$;

$R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ are independently chosen from hydrogen, hydrocarbyl, substituted hydrocarbyl, halogen, hydroxyl, SH, $SR^{1811}$, $OR^{1811}$, and $NR^{1811}R^{1812}$, wherein any pair of $R^{\#a}$ and $R^{\#b}$ where # is chosen from 7, 8, 10, 15, and 16 may be optionally linked by groups chosen from =O, =S, and =$NR^{1813}$;

$R^{17}$ is chosen from hydrocarbyl or substituted hydrocarbyl;

$R^{1811}$, $R^{1812}$, and $R^{1813}$ are independently chosen from hydrogen, hydrocarbyl, and substituted hydrocarbyl;

the dashed lines between the C-7 and C-8 carbons represent a carbon-carbon double bond or a carbon-carbon single bond, provided that if there is a double bond between the C-7 and C-8 carbons then only one of $R^{7a}$ and $R^{7b}$ is present and only one of $R^{8a}$ or $R^{8b}$ is present; and provided that one or more of $R^1$, $R^2$, $R^3$, $R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ may be linked to form carbocyclic or heterocyclic rings.

In still another aspect, the present disclosure provides a one pot process for producing a compound comprising Formula (Ia) from a compound comprising Formula (IIa). The process comprises (a) contacting the compound comprising Formula (IIa) with an alkylating reagent comprising $R^{17}$ to form an intermediate comprising Formula (IIIa), wherein the intermediate comprising Formula (IIIa) is not isolated; and (b) contacting the intermediate comprising Formula (IIIa) with a reducing agent and a proton acceptor to form the compound comprising Formula (Ia) according to the following reaction scheme:

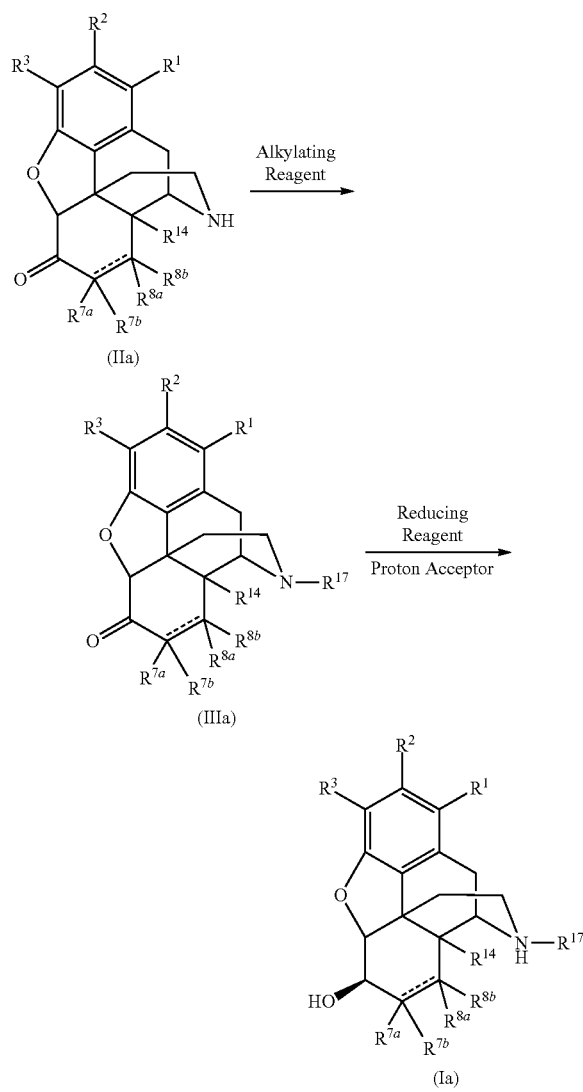

wherein, $R^1$, $R^2$, and $R^3$ are independently chosen from hydrogen, hydrocarbyl, substituted hydrocarbyl, halogen, hydroxyl, SH, $SR^{1811}$, $OR^{1811}$, and $NR^{1811}R^{1812}$;

$R^{7a}$, $R^{7b}$, $R^{8a}$, and $R^{8b}$ are independently chosen from hydrogen, hydrocarbyl, substituted hydrocarbyl, halogen, hydroxyl, SH, $SR^{1811}$, $OR^{1811}$, and $NR^{1811}R^{1812}$, wherein any pair of $R^{\#a}$ and $R^{\#b}$ where # is chosen from 7 and 8 may be optionally linked by groups chosen from =O, =S, and =$NR^{1813}$;

$R^{14}$ is chosen from hydrogen, hydroxyl, and $OR^{1811}$;

$R^{17}$ is chosen from hydrocarbyl or substituted hydrocarbyl;

$R^{1811}$, $R^{1812}$, and $R^{1813}$ are independently chosen from hydrogen, hydrocarbyl, and substituted hydrocarbyl;

the dashed lines between the C-7 and C-8 carbons represent a carbon-carbon double bond or a carbon-carbon single bond, provided that if there is a double bond between the C-7 and C-8 carbons then only one of $R^{7a}$ and $R^{7b}$ is present and only one of $R^{8a}$ or $R^{8b}$ is present; and provided that one or more of $R^1$, $R^2$, $R^3$, $R^{7a}$, $R^{7b}$, $R^{8a}$, $R^{8b}$, and $R^{14}$ may be linked to form carbocyclic or heterocyclic rings Other features and iterations of the disclosure are described in more detail herein.

DETAILED DESCRIPTION OF THE INVENTION

Briefly, therefore, the present invention relates to a process of producing opiate alkaloids where no intermediates are isolated. The choice of reagents, solvent, and extraction conditions avoid the need for the isolation of reaction intermediates. As used herein, a process where no intermediates are isolated means a process free of steps where structures on the synthetic pathway to the desired opiate alkaloid, are removed from the reaction mixture. The invention has further advantages of proceeding in high yields, tolerating a variety of functional groups on the opiates, and giving high ratios of the desired epimers or enantiomers.

The products of the reaction generally comprise opiate alkaloids which have the general structure below. The fused ring structure shows the numbering associated with individual atoms of the alkaloid ring structure.

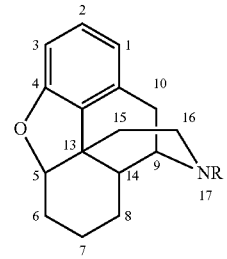

The core structure can be substituted as described herein and shown in various figures. These compounds are recognized to have an alpha face and a beta face. Some compounds described herein, may have at least four chiral centers, namely carbons C-5, C-9, C-13, and C-14, and provided that the C-15 and C-16 atoms are both on the alpha face of the molecule or both on the beta face of the molecule. Additionally, when C-6 is substituted with a singly bonded substituent, C-6 may be a chiral center. At each chiral center, the stereochemistry at the carbon atom is independently R or S.

(I) Process for Producing 6-Hydroxyl Nal-Opiates from 6-Keto Nor-Opiates

One aspect of the invention encompasses a process for the production of a 6-hydroxyl nal-opiate from a 6-keto nor-opiate. The process comprises contacting the 6-keto nor-opiate to produce a 6-keto nal-opiate. The 6-keto nal-opiate is not isolated in the process, and the reaction mixture resulting from the contacting of the 6-keto nor-opiate comprising the 6-keto nal-opiate is reacted directly with a reducing agent to produce the 6-hydroxyl nal-opiate. Advantageously, the steps of the process may be conducted in tandem, in a single pot, without isolation of any reaction intermediates including the 6-keto nal-opiate.

(II) Process for Producing a Compound Comprising Formula (I) from a Compound Comprising Formula (II)

In another embodiment, the opiate of the compound comprising Formula (I) is prepared from a compound comprising Formula (II). The process comprises a first step (Step A) of contacting the compound comprising Formula (II) with an alkylating reagent to form the intermediate comprising Formula (III). Without isolating the intermediate comprising Formula (III), it is then contacted with a reducing agent in a second step (Step B). The reduction step can proceed directly from the crude reaction mixture formed by the contacting of the compound comprising Formula (II) with the alkylating reagent. For purposes of illustration, Reaction Scheme 1 depicts the process of producing the compound comprising Formula (I) in accordance with this aspect of the invention:

Reaction Scheme 1:

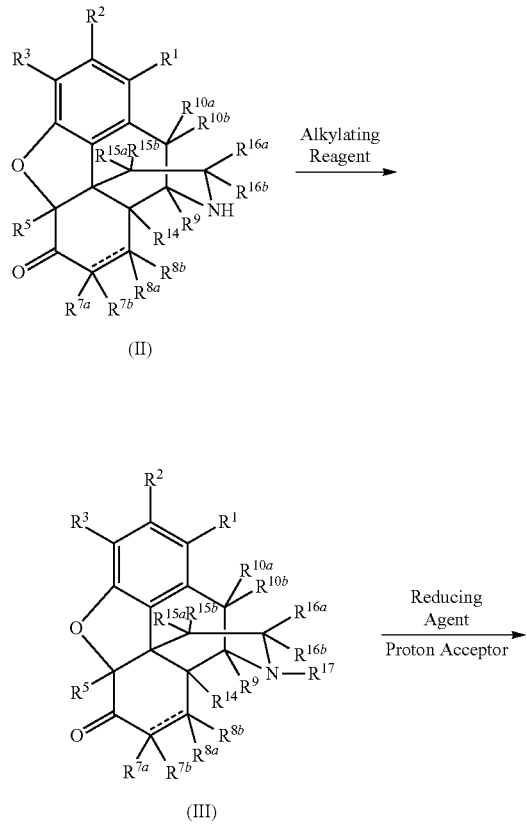

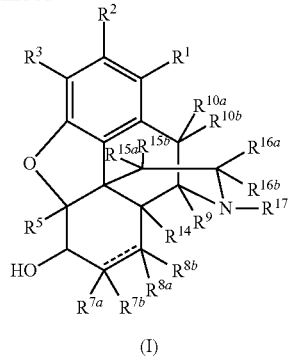

(I)

wherein, $R^1$, $R^2$, and $R^3$ are independently chosen from hydrogen, hydrocarbyl, substituted hydrocarbyl, halogen, hydroxyl, SH, $SR^{1811}$, $OR^{1811}$, and $NR^{1811}R^{1812}$;

$R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ are independently chosen from hydrogen, hydrocarbyl, substituted hydrocarbyl, halogen, hydroxyl, SH, $SR^{1811}$, $OR^{1811}$, and $NR^{1811}R^{1812}$, wherein any pair of $R^{\#a}$ and $R^{\#b}$ where # is chosen from 7, 8, 10, 15, and 16 may be optionally linked by groups chosen from =O, =S, and =$NR^{1813}$;

$R^{17}$ is chosen from hydrocarbyl or substituted hydrocarbyl;

$R^{1811}$, $R^{1812}$, and $R^{1813}$ are independently chosen from hydrogen, hydrocarbyl, and substituted hydrocarbyl;

the dashed lines between the 0-7 and C-8 carbons represent a carbon-carbon double bond or a carbon-carbon single bond, provided that if there is a double bond between the C-7 and C-8 carbons then only one of $R^{7a}$ and $R^{7b}$ is present and only one of $R^{8a}$ or $R^{8b}$ is present; and provided that one or more of $R^1$, $R^2$, $R^3$, $R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ may be linked to form carbocyclic or heterocyclic rings.

In some embodiments, $R^1$, $R^2$, $R^5$, $R^{7a}$, $R^{7b}$, $R^{8a}$, $R^{8b}$, $R^9$, $R^{10a}$, $R^{10b}$, $R^{15a}$, $R^{15b}$, $R^{16a}$, and $R^{16b}$ are each hydrogen. In another embodiment, there is a carbon-carbon double bond between the C-7 and C-8 carbons and $R^{7a}$ and $R^{8a}$ are hydrogen. In still another embodiment, $R^3$ is chosen from hydrogen, alkyl, alkenyl, aryl, substituted alkyl, substituted alkenyl, substituted aryl, acyl, alkoxycarbonyl, aroxycarbonyl, acetal, ether, silyl ether, and alkylsulfonyl. Preferably, $R^3$ is hydrogen, hydroxyl, or $OR^{1811}$.

$R^{1811}$, $R^{1812}$, and $R^{1813}$ may be independently chosen from hydrogen, hydrocarbyl or substituted hydrocarbyl. In some embodiments, $R^{1811}$, $R^{1812}$, and $R^{1813}$ are alkyl groups containing from 1 to 6 carbons. In a preferred embodiment, $R^{1811}$, $R^{1812}$, and $R^{1813}$ are independently chosen from methyl or ethyl.

In some embodiments, $R^{17}$ may be an alkyl group, an alkenyl group, or an alkaryl group. In some embodiments, $R^{17}$ is a hydrocarbyl or substituted hydrocarbyl containing between 1 and 20 carbon atoms, more preferably between 1 and 6 carbon atoms. In still other embodiments, the $R^{17}$ group may be an alkyl group including methyl, ethyl, propyl, isopropyl, butyl, sec-butyl, isobutyl, tert-butyl, propyl, isopropyl, sec-propyl, and the like. In another embodiment, the $R^{17}$ group may be an alkenyl group including allyl, methallyl, and the like. In still another embodiment, the $R^{17}$ group comprises a cyclic compound including methanecyclopropyl, methanecyclobutyl, methanecyclopentyl, methanecyclohexyl, and the like. In a preferred embodiment, $R^{17}$ is chosen from methyl, allyl, methanecyclopropyl, methanecyclobutyl.

In one embodiment, $R^1$, $R^2$, $R^5$, $R^{7a}$, $R^{7b}$, $R^{8a}$, $R^{8b}$, $R^9$, $R^{10a}$, $R^{10b}$, $R^{15a}$, $R^{15b}$, $R^{16a}$, and $R^{16b}$ are each hydrogen. In another embodiment, $R^3$ and $R^{14}$ are chosen from hydroxyl and $OR^{1811}$. In still another embodiment $R^{17}$ is chosen from methyl allyl, methanecyclopropyl, and methanecyclobutyl.

In one preferred embodiment, $R^1$, $R^2$, $R^5$, $R^{7a}$, $R^{7b}$, $R^{8a}$, $R^{8b}$, $R^9$, $R^{10a}$, $R^{10b}$, $R^{15a}$, $R^{15b}$, $R^{16a}$, and $R^{16b}$ are each hydrogen; $R^3$ and $R^{14}$ are each hydroxyl; and $R^{17}$ is allyl.

(a) Step A of the Process

Step A includes alkylation of the compound comprising Formula (II) with an alkylating reagent which forms a reaction mixture containing the intermediate comprising Formula (III). The components and reaction conditions are described below.

(I) Alkylation Reagent

Step A comprises and alkylation reagent that reacts with the opiate alkaloid to alkylate the N-17 position. Suitable alkylation reagents may comprise $R^{17}$ and an acceptable leaving group. The alkylation reagent is capable of imparting the $R^{17}$ group to the compound comprising Formula (II). In some embodiments, $R^{17}$ is a hydrocarbyl or substituted hydrocarbyl containing between 1 and 20 carbon atoms, more preferably between 1 and 6 carbon atoms. In still other embodiments, the $R^{17}$ group may be an alkyl group including methyl, ethyl, propyl, isopropyl, butyl, sec-butyl, isobutyl, tert-butyl, propyl, isopropyl, sec-propyl, and the like. In other embodiments, the $R^{17}$ group may be an alkenyl group including allyl, methallyl, and the like. In still another embodiment, the $R^{17}$ group comprises a cyclic structure including methanecyclcopropyl, methanecyclobutyl, methanecyclopentyl, methanecyclohexyl and the like. In a preferred embodiment, $R^{17}$ is chosen from methyl, allyl, methanecyclopropyl, and methanecyclobutyl.

The leaving group may be chosen from any leaving group known in the art so long as alkylation reagent is capable of imparting $R^{17}$. Non-limiting examples of acceptable leaving groups include triflates, tosylates, mesylates, halogens (including iodides, bromides, and chlorides), hydroxyl, acyl groups, and the like. In preferred embodiments, the leaving group is a halogen chosen from bromide or chloride. Exemplary alkylation reagents include alkyl or alkenyl halides such as methylbromide, allylbromide, methanecyclopropylbromide, methanecyclobutylbromide, and the like.

The amount of alkylation reagent may vary but generally is present in a mole-to-mole ratio of the compound comprising Formula (II) to alkylating reagent of about 1:0.1 to about 1:10. In another embodiment, the mole-to-mole ratio of the compound comprising Formula (II) to the alkylating reagent may range from about 1:0.8 to about 1:5, or more preferably, is about 1:1.1.

(ii) Proton Acceptor

In some embodiments, Step A further comprises contacting the compound comprising Formula (II) with a proton acceptor. In general, the proton acceptor has a pKa of between about 7 and about 13, more preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), alkyl amine bases (such as, for example, triethylamine, trimethylamine, tributylamine, diethylamine, and diisopropylethylamine), organic bases (such as, for example, pyridine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino)ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. In an exemplary embodiment, the proton acceptor may be sodium bicarbonate.

The mole-to-mole ratio of the compound comprising Formula (II) to the proton acceptor may range from about 1:0.1 to about 1:20. In a preferred embodiment, the mole-to-mole ratio of the compound comprising Formula (II) to the proton acceptor may range from about 1:5 to about 1:10. In an exemplary embodiment, the mole-to-mole ratio of the compound comprising Formula (II) to the proton acceptor may be about 1:2.

(iii) Solvent

Step A may further comprise an organic solvent which is preferably an aprotic solvent. Non-limiting examples of suitable organic solvents include acetonitrile, acetone, benzene, chlorobenzene, chloroform, chloromethane, cyclohexane, cyclopentane, dichloromethane (DCM), dichloroethane, dimethylacetamide, dimethyl formamide (DMF), dimethyl sulfonic acid (DMSO), dioxane, 1,3-dimethyl-1,3,4,5,6-tetrahydro-2(1H)-pyrimidinone (DMPU), 1,3-dimethyl-2-imidizolinone (DMI), 1,2-dimethoxyethane (DME), dimethylacetamide (DMA), ethylene bromide, fluorobenzene, hexamethylphosphoramide, heptane, hexane, isobutylmethylketone, N-methylpyrrolidinone (NMP), methylene bromide, methylethylketone, methylbutylether, methyltetrahydrofuran, pentane, tetrahydrofuran, tetrachloroethane, toluene, xylene and the like. In preferred embodiments, the organic solvent is chosen from dimethyl formamide, N-methylpyrrolidinone, and dimethylacetamide.

In some embodiments, Step A may comprise one or more organic solvents. When one or more organic solvents are present in the reaction the solvents may be present in any ratio without limitation. In some embodiments, one or more solvents may be present in Step A in approximately an equal ratio by weight. In another embodiment, one solvent may be present in an excess. Where there are two solvents, the solvents may be present in a weight to weight (wt/wt) ratio of about 1:0.01, 1:0.1, 1:0.5, 1:0.9, 1:1, 1:1.5, 1:2, or 1:3. When more than two solvents are present, the ratios may vary similarly.

The amount of organic solvent present in Step A can and will vary. In some aspects, the starting amount of the compound comprising Formula (II) and the organic solvent may be present in a (wt/wt) ratio of ranging from 1:0.5 to 1:50. In another embodiment, the starting amount of the compound comprising Formula (II) and the organic solvent are present in a (wt/wt) ratio of about 1:10. In a preferred embodiment the starting amount of the compound comprising Formula (II) and the organic solvent may be present in a (wt/wt) ratio of about 1:2.5.

(iv) Reaction Conditions

The temperature at which the Step A is conducted can vary in different embodiments and over the course of the reaction. In some aspects, Step A is conducted at a temperature of about 0° C., 10° C., 15° C., 20° C., 25° C., 30° C., 35° C., 40° C., 50° C., 60° C., 70° C., 80° C., 90° C., 100° C. or at a range between and including any two of these values. In one embodiment, the reaction is carried out at a temperature ranging from about 5° C. and about 50° C. In another embodiment, the temperature may range from about 15° C. and about 40° C. In an exemplary embodiment, Step A is conducted at about 18° C. to 25° C. Generally, Step A is performed under ambient pressures. In some embodiments, Step A is conducted in an inert atmosphere such as nitrogen or argon.

The duration of Step A can and will vary. In general, Step A may be allowed to proceed from several hours to several days. Typically, however, Step A is allowed to proceed for a sufficient period of time until the reaction is complete, as determined by means known to those of skill in the art. In this context, the reaction mixture contains a significantly diminished amount of the compound comprising Formula (II) and a significantly increased amount of the intermediate comprising Formula (III) compared to the amounts of each present at the beginning of the reaction. In some embodiments, Step A may be allowed to proceed for a period of time ranging from about 1 hour to about 2 days. In one preferred embodiment, Step A is allowed to proceed for about 16 hours.

(v) Precipitation

In some embodiments, the process further comprises a precipitation step, which may occur during Step A or after the completion of Step A. Precipitation occurs with the addition of a protic solvent to the reaction mixture formed by contacting the compound comprising Formula (II) with the alkylating reagent. Examples of suitable protic solvents include, without limit, water, C1-C4 alcohols (including methanol, ethanol, isopropanol, n-propanol, isobutanol, n-butanol, s-butanol, t-butanol, and the like), a diol such as propylene glycol, formic acid, acetic acid and mixtures thereof. In a preferred embodiment, the protic solvent is water.

The amount of protic solvent added to the reaction mixture can and will vary. In some aspects, the compound comprising Formula (II) and the protic solvent may be present in a (wt/wt) ratio of ranging from 1:0.5 to 1:50. In another embodiment, the compound comprising Formula (II) and the protic solvent may be present in a (wt/wt) ratio of about 1:10. In a preferred embodiment the compound comprising Formula (II) and the protic solvent may be present in a (wt/wt) ratio of about 1:5.

Additional alkylating reagent may be added with or after the protic solvent to react with any of the compound comprising Formula (II) which is unreacted. The additional alkylating reagent is generally added in a mole-to-mole ratio with respect to the starting amount of the compound comprising Formula (II) ranging from about 0.001:1 to about 0.1:1.

Without being bound to any theory, the protic solvent precipitates the compound comprising Formula (III) which leaves any unreacted compound comprising Formula (II) left in the solution to react with excess or additional alkylating reagent. Excess alkylating reagent may also be destroyed by the protic solvent. This provides an increased yield of the intermediate comprising Formula (III). In some aspects, the unisolated yield the compound comprising Formula (III) may be above 75%, 80%, 90%, or above 95%.

(b) Step B of the Process

Step B proceeds directly from the reaction mixture of Step A and the process generally involves reduction with a reducing agent and a proton acceptor to form the compound comprising Formula (I).

(i) Reducing Agent

In general, the reducing agent is an agent for chemical reduction. The reducing agent is contacted directly with the reaction mixture produced in Step A. Suitable reducing agents for the reduction of the intermediate comprising Formula (III) include sulfinic acids, hydrosulphites, borohydride reagents and aluminum hydrides, (preferably bulky reagents borohydride aluminum hydride reagents such as, for example, LiAl(O-t-Bu)$_3$H, or 9-borabycyclo[3.3.1]nonane), catalytic hydrogen transfer reduction regents. Hydrogen transfer reduction agents generally comprise a transition metal and a hydrogen donor. Transition metals may be chosen from, for example, ruthenium, iridium, palladium, platinum, or rhodium. Hydrogen donors are known in the art and include, for example, H$_2$CO$_2$H, or a H$_2$CO$_2$H-amine complex. Hydrogen transfer reagents may further comprise a ligand. In some embodiments, reduction occurs with a RuCl (TsDPEN)(n-6-cymene) catalyst. Sulfinic acids include formamidine sulfinic acid and hydroxymethane sulfinic acid. An exemplary sulfininc acid reducing agent is formamidine sulfinic acid. Hydrosulphites may include hydrosulphites comprising various counterions including sodium, lithium, potassium, and the like. An exemplary hydrosulphite is sodium hydrosulphite.

The amount of reducing agent added may vary. In some aspects the amount of reducing agent can be measured against the starting amount of the compound comprising Formula (II). In such embodiments, the mole-to-mole ratio of the starting amount of the compound comprising Formula (II) and the reducing agent may be added in amount ranging from about 0.1:1 to about 1:20. More preferably, the mole-to-mole ratio of the starting amount of the compound comprising Formula (II) to the reducing agent may range from about 1:5 to about 1:10. In an exemplary embodiment, the mole-to-mole ratio of the compound comprising Formula (II) to the proton acceptor may be about 1:2. In some embodiments, the ratio of the starting amount of the compound comprising Formula (II) to the alkylating reagent to the reducing agent is about 1:1.1:4.

In some embodiments, the reducing agent tolerates sensitive chemical functionalities such as amines, amides, sulfides, thiols and the like. That is, the reducing agent reacts predominantly at the C-6 position and does not affect other chemical functionalities that may be present on the opiate alkaloid. The selectivity of the reducing agent results in a higher yield of the desired product. In further embodiments, the choice of reagent can give a particular α- or β-configuration of the reduced carbon. In some embodiments, sufinic acids and hydrosulphites give the β-configuration at the C-6 position. In other embodiments, aluminum hydride, borohydride and catalytic transfer reduction agents give the α-configuration at the C-6 position.

(ii) Proton Acceptor

Step B further comprises a proton acceptor. The proton acceptor may be chosen from those listed in section (II)(a)(ii). In one exemplary embodiment, the proton acceptor is sodium hydroxide. The proton acceptor may be added as an aqueous solution. In some embodiments, the aqueous solution may range from a 10% aqueous solution to about a 50% aqueous solution. More preferably, the aqueous solution is a 10% aqueous solution, a 15% aqueous solution, a 20% aqueous solution, a 25% aqueous solution, a 30% aqueous solution, a 35% aqueous solution, a 40% aqueous solution, a 45% aqueous solution, or a 50% aqueous solution.

In a preferred embodiment, the proton acceptor is a sodium hydroxide proton acceptor in a 25% aqueous solution which is added to the reaction mixture in a (wt/wt) ratio of about 1:5 of the starting amount of the compound comprising Formula (II) to the sodium hydroxide solution, respectively.

(iii) Reaction Conditions

The conditions for Step B can vary without departing from the scope of the invention depending on the reducing agent used as well as other factors. In some embodiments, Step B may be performed at a temperature ranging from about 10° C. to about 120° C. In some embodiments, Step B is conducted at a temperature ranging from about 40° C. to about 70° C. In alternate embodiments, the Step B is conducted at a temperature ranging from about 70° C. to 100° C. In various embodiments, Step B may be conducted at about 10° C., 20° C., 30° C., 40° C., 50° C., 60° C., 70° C., 80° C., 90° C., 100° C., 110° C., or 120° C., or at a temperature between and including any of the listed temperatures. In one preferred embodiment Step B may be performed at about 60° C. Generally, Step B is conducted under ambient pressures. In some embodiments, Step B is conducted under an inert atmosphere, for example, of argon or nitrogen.

The duration of Step B can and will vary. In general, Step B may be allowed to proceed from several hours to several days. Typically, however, Step B is allowed to proceed for a sufficient period of time until the reaction is complete, as determined by means well known to those of skill in the art. In this context, the reaction mixture contains a significantly diminished amount of the intermediate comprising Formula (III) and a significantly increased amount of the compound comprising Formula (I) compared to the amounts of each present at the beginning of Step B. In some embodiments, Step B may be allowed to proceed for a period of time ranging from about 1 hour to about 2 days. In one preferred embodiment, Step B is allowed to proceed for about 6 hours.

(iv) Stereochemistry

The compounds comprising any of Formulas (I), (II) or (III) may have a (−) or a (+) orientation with respect to the rotation of polarized light. More specifically, each chiral center of the morphinans may have an R or an S configuration. The compound comprising Formula (II) or the intermediate comprising Formula (III) may have four chiral centers, namely carbons C-5, C-9, C-13, and C-14. The configurations of C-5, C-9, C-13, and C-13, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

The compounds comprising Formula (I) may have at least five chiral centers, namely, the C-5, C-6, C-9, C-13, and C-14 carbons. The configuration of C-5, C-6, C-9, C-13, and C-14, respectively, may be RRRRR, RSRRR, RRRRS, RSRRS, RRRSR, RSRSR, RRSRR, RSSRR, SRRRR, SSRRR, RRRSS, RSRSS, RRSSR, RSSSR, SRSRR, SSSRR, SRRRS, SSRRS, SRRSR, SSRSR, RRSRS, RSSRS, RRSSS, RSSSS, SRRSS, SSRSS, SRSRS, SSSRS, SRSSR, SSSSR, SRSSS, and SSSSS, respectively, provided that the C-15 and the C-16 carbons are both either on the alpha face of the molecule or the beta face of the molecule. The reaction product may be a racemic mixture or may be enriched with compounds having one or more configurations. In some embodiments, the process provides a particular configuration of the compound comprising Formula (I) in an amount of greater than 65% of the total reaction yield, greater than 75% of the total reaction yield, greater than 85% of the total reaction yield, greater than 95% of the total reaction yield, or greater than 99% of the total reaction yield.

In one aspect, the process includes formation of an additional chiral center at C-6. Upon reduction, the C-6 carbon becomes a chiral center. In some aspects, the process provides for a particular configuration in a ratio greater than other possible configurations. In general, the processes may give an alpha or beta configuration at the C-6 carbon. In some embodiments, the process produces one configuration in an amount ranging from about 80% to 100% of the total yield. In some embodiments, the beta configuration is produced in a ratio of greater than 80:20 to the alpha configuration. In still other embodiments, the beta configuration is produced in a ratio of greater than 85:15, 90:10, 95:5, 97:3, 98:2, 99:1 or 99.5:0.5 to the alpha configuration. In still further embodiments, the alpha configuration is produced in a ratio of greater than 80:20 to the beta configuration. In another alternative embodiment the alpha configuration is produced in a ratio greater than 85:15, 90:10, 95:5, 97:3, 98:2, 99:1 or 99.5:0.5 to the beta configuration.

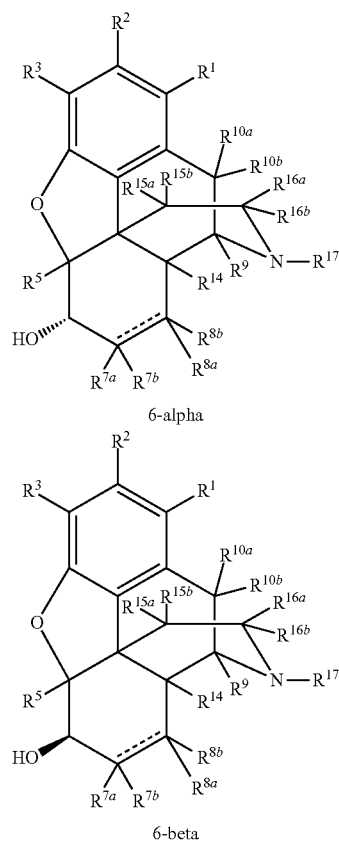

6-alpha 6-beta (v) Compound Comprising Formula (I)

The yield of the compound comprising Formula (I) can and will vary. Typically, the yield of the compound comprising Formula (I) may be at least about 50%. In one embodiment, the yield of the compound comprising Formula (I) may range from greater than about 55% to about 75%. In another embodiment, the yield of the compound comprising Formula (I) may be greater than about 60% or about 75%. In a further embodiment, the yield of the compound comprising Formula (I) may be above about 80%.

The compounds comprising Formula (I) may be optionally purified by any means known in the art. In various aspects, the compound comprising Formula (I) may be purified by chromatography, precipitation, crystallization or any other acceptable method. The compounds may be obtained in a purity greater than 80%, 90%, 95%, or 99%. In preferred embodiments, the compound comprising Formula (I) is precipitated with a base under temperatures ranging from about 0° C. to about 15° C. and the precipitated solids are washed with water and dried in an oven.

Exemplary compounds comprising Formula (I), without limitation, are provided below. As described herein, the compounds may be of any configuration described herein including alpha or beta configurations at the 6-carbon.

(II) Process for Producing a Compound Comprising Formula (Ia) from a Compound Comprising Formula (IIa)

A further aspect of the invention encompasses a process in which an opiate comprising Formula (Ia) is prepared from a compound comprising Formula (IIa), as detailed above in sections (II)(a) and (b). Briefly, the compound comprising Formula (IIa) is contacted with an alkylating reagent to form the intermediate comprising Formula (IIIa). The process further comprises contacting the intermediate comprising Formula (IIIa), without isolation, with a reducing agent to form the compound comprising Formula (Ia) in accordance with Reaction Scheme 2:

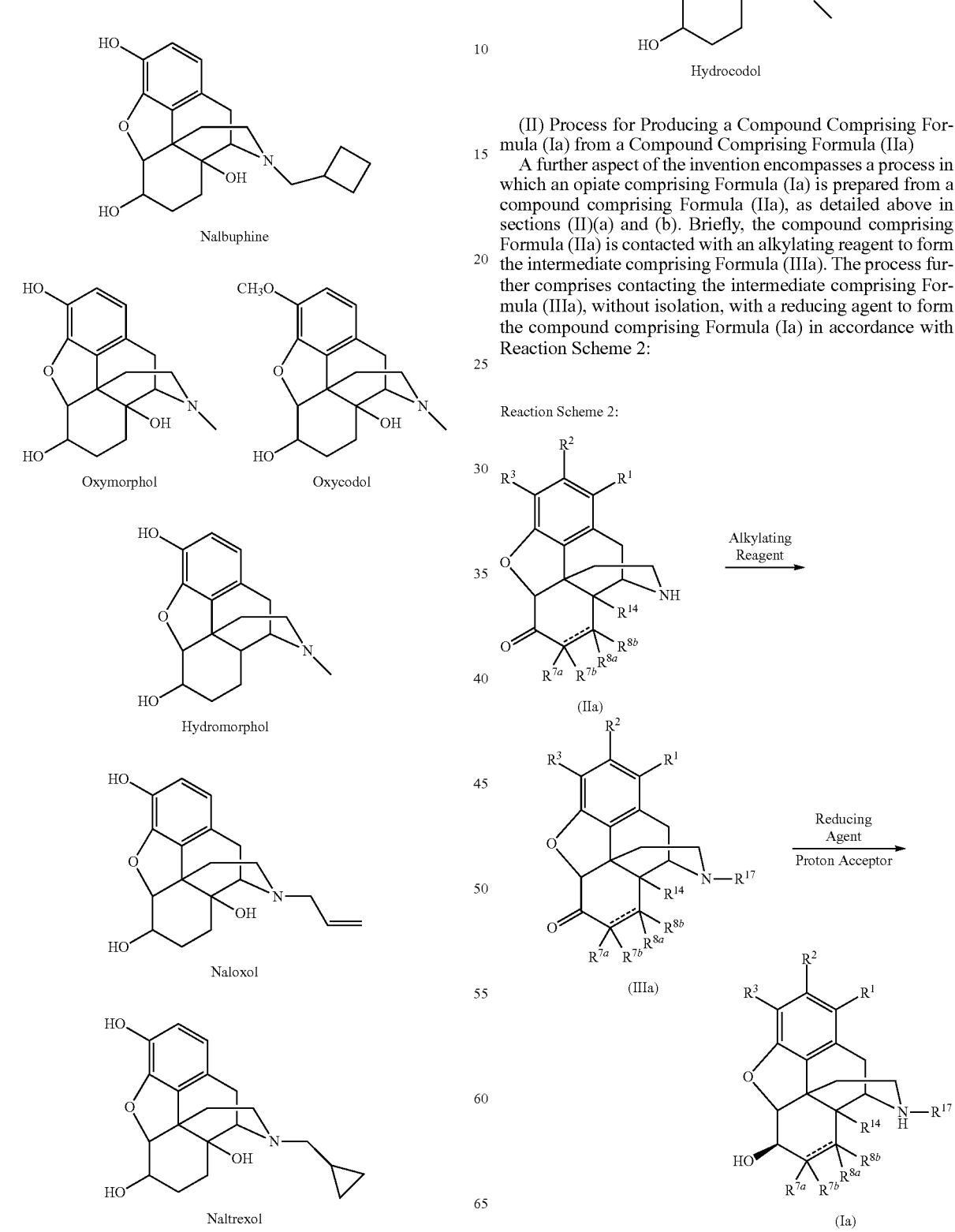

Reaction Scheme 2:

wherein, $R^1$, $R^2$, and $R^3$ are independently chosen from hydrogen, hydrocarbyl, substituted hydrocarbyl, halogen, hydroxyl, SH, $SR^{1811}$, $OR^{1811}$, and $NR^{1811}R^{1812}$;

$R^5$, $R^{7a}$, $R^{7b}$, $R^{8a}$, $R^{8b}$, $R^9$, $R^{10a}$, $R^{10b}$, $R^{14}$, $R^{15a}$ $R^{15b}$, $R^{16a}$, and $R^{16b}$ are independently chosen from hydrogen, hydrocarbyl, substituted hydrocarbyl, halogen, hydroxyl, SH, $SR^{1811}$, $OR^{1811}$, and $NR^{1811}R^{1812}$, wherein any pair of $R^{\#a}$ and $R^{\#b}$ where # is chosen from 7, 8, 10, 15, and 16 may be optionally linked by groups chosen from =O, =S, and =$NR^{1813}$;

$R^{17}$ is chosen from hydrocarbyl or substituted hydrocarbyl;

$R^{1811}$, $R^{1812}$, and $R^{1813}$ are independently chosen from hydrogen, hydrocarbyl, and substituted hydrocarbyl;

the dashed lines between the C-7 and C-8 carbons represent a carbon-carbon double bond or a carbon-carbon single bond, provided that if there is a double bond between the C-7 and C-8 carbons then only one of $R^{7a}$ and $R^{7b}$ is present and only one of $R^{8a}$ or $R^{8b}$ is present; and provided that one or more of $R^1$, $R^2$, $R^3$, $R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ may be linked to form carbocyclic or heterocyclic rings.

In some embodiments $R^2$, $R^{7a}$, $R^{7b}$, $R^{8a}$ and $R^{8b}$ are hydrogen. In other embodiments, $R^3$ and $R^{14}$ are hydroxyl. In still other embodiments, $R^{17}$ is chosen from methyl, allyl, methanecyclopropyl, and methanecyclobutyl.

In one exemplary embodiment, $R^2$, $R^{7a}$, $R^{7b}$, $R^{8a}$, and $R^{8b}$ are hydrogen; $R^3$ and $R^{14}$ are hydroxyl; the bond between C-7 and C-8 is a carbon-carbon single bond; and $R^{17}$ is allyl.

In another exemplary embodiment, $R^{7a}$, $R^{7b}$, $R^{8a}$, and $R^{8b}$ are hydrogen; $R^3$ is $OR^{1811}$; $R^{14}$ is hydrogen; the bond between C-7 and C-8 is a carbon-carbon single bond; $R^{17}$ is chosen from methyl, allyl, methanecyclopropyl, and methanecyclobutyl; and $R^{1811}$ is methyl.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is $R^1$, $R^1$O—, $R^1R^2$N—, or $R^1$S—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

Having described the invention in detail, it will be apparent that modifications and variations are possible without departing from the scope of the invention defined in the appended claims.

EXAMPLES

Example 1

Conversion of a Noroxymorphone to 6-β-Naloxol in One Pot

Noroxymorphone was produced by according to the following reaction scheme:

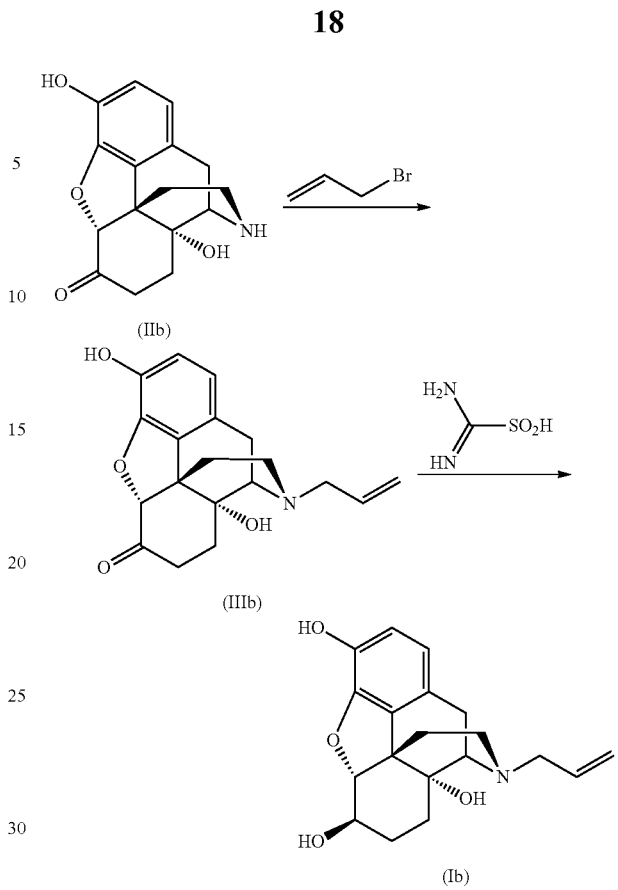

A mixture of (IIb) (50.0 g), sodium bicarbonate (29.2 g) and N-methyl-2-pyrrolidine (125 mL) were added to a flask. The contents of the flask were stirred under nitrogen at room temperature (18-25° C.). Allyl bromide (22 g) was added. The above suspension was stirred at 30° C. for more than 16 hours. Water (250 g) was added to form a suspension. 3 g of allyl bromide was added. The resulting suspension was allowed to stir at 30° C. for more than 12 hours to form (IIIb) Formamideinesulfonic acid (75 g) a sodium hydroxide solution (25% in water, 250 g) were added. The reaction mixture was stirred at room temperature for 1 hour, then heated to 60° C. for over 1 hour, then maintained at 60° C. for 6 hours. The pH of the reaction mixture was then adjusted to 9.5 to form a precipitate. The resulting suspension was cooled down to 10° C. for 1 hour and filtered. The solids obtained were washed with water (3×50 g). The wet solids were dried at 65° C. in a vacuum oven overnight to give 40-45 g (Ib).

Example 2

Reduction of Naloxone with Sodium Hydrosulphite

Naloxone.HCl (11.1 g, 30.5 mmol)) and $Na_2S_2O_4$ (10.6 g, 61 mmol) were added to a flask. Sodium hydroxide (10%, 80 g) was added with stirred under nitrogen. The mixture was heated to 60° C. for 6 hours. The pH of the reaction mixture was adjusted to 10 with $NH_4Cl$ to precipitate out the product. The suspension was cooled down to 10° C. and stirred at 10° C. for 2 hours and filtered. The solids obtained were washed with water (2×10 mL) and dried in oven at 65° C. for 18 hours to give 8.86 g of dry solids of 6-beta-naloxol base.

Example 3

Reduction of (−)-Hydrocodone with Sodium Hydrosulphite

Hydrocodone base (5.0 g, 15.9 mmol) and $Na_2S_2O_4$ (5.5 g, 31.8 mmol) were added to a flask. Sodium hydroxide (10%, 80 g) was added with stirred under nitrogen. The mixture was heated to 60° C. for 9 hours. The pH of the reaction mixture was adjusted to 10 with $NH_4Cl$ to precipitate out the product. The suspension was cooled down to 10° C. and stirred at 10° C. for 2 hours and filtered. The solids obtained were washed with water (2×10 mL) and dried in oven at 65° C. for 18 hours to give 3.0 g of dry solids of 6-beta-hydrocodol base.

Example 4

Reduction of (+)-Hydrocodone with Sodium Hydrosulphite (+)-Hydrocodone base (1.0 g, 3.2 mmol), $Na_2CO_3$ (3 g), and $Na_2S_2O_4$ (1.1 g, 6.4 mmol) were added to a flask. NMP (5 g) and water (5 g) were added with stirred under nitrogen until the desired pH was reached. The mixture was heated to 60° C. for 9 hours. The suspension was diluted with water (10 g), cooled down to 10° C., stirred at 10° C. for 2 hours and filtered. The solids obtained were washed with water (2×3 mL) and dried in oven at 65° C. for 18 hours to give 0.51 g of dry solids of (+)-6-beta-hydrocodol base.

Example 5

Reduction of (+)-Hydromorphone with Sodium Hydrosulphite

Hydromorphone base (5.0 g, 15.9 mmol) and $Na_2S_2O_4$ (5.5 g, 31.8 mmol) were added to a flask. Sodium hydroxide (10%, 80 g) was added with stirred under nitrogen. The mixture was heated to 60° C. for 9 hours. The pH of the reaction mixture was adjusted to 10 with $NH_4Cl$ to precipitate out the product. The suspension was stirred at 10° C. for 2 hours and filtered. The solids obtained were washed with water (2×10 mL) and dried in oven at 65° C. for 18 hours to give 3.3 g of dry solids of 6-beta-hydromorphol base.

Example 9

Reduction of (+)-Hydromorphone with Sodium Hydrosulphite

Noroxymorphone will be produced by according to the following reaction scheme:

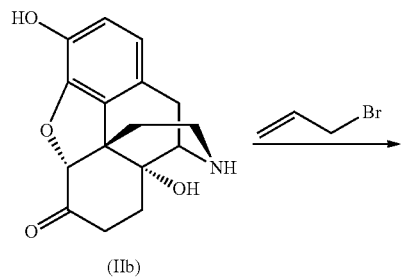

(IIb)

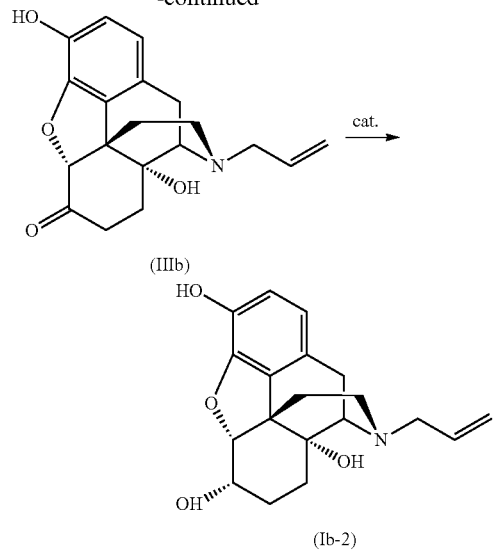

A mixture of (IIb) (50.0 g), diisopropyethylamine (33.5 g) and N-methyl-2-pyrrolidine (125 mL) will be added to a flask. The contents of the flask will be stirred under nitrogen at room temperature (18-25° C.). Allyl bromide (23 g) will be added.

The above suspension will be stirred at 28° C. for more than 18 hours. The completeness of the alkylation of IIb to form IIIb will be monitored by HPLC analysis. Additional allyl bromide will be added if needed to complete the reaction.

Formic acid (51.7 g) and triethylamine (35 g) will be added slowly while maintaining the reaction mixture at <31° C. with ice bath. The mixture will be cooled down to 0-5° C. Catalyst of [RuCl(TsDPEN)(η-6-cymene)] (1 g) (TsDPEN=$H_2$NCHPhCHPhNTs-=(S,S)-1,2-diphenyl-N-tosyl-1,2-ethanediaminato) will be added under nitrogen. The resulting mixture will be allowed to stir at 20° C. overnight and will be slowly heated to 50° C. until the reaction is completed as monitored by HPLC analysis. Water (800 mL) will be added to form a solution. The pH of the solution will be adjusted to 9.5 with c-$NH_4OH$ to form precipitate. The resulting suspension will be cooled down to 10° C. for 1 hour and filtered. The solids obtained will be washed with water (4×50 g). The wet solids will be dried at 65° C. in a vacuum oven overnight to give an estimated 35-45 g of (Ib-2). The ratio of 6-α-naloxo to 6-β-naloxol is expected to be >98:2 or 99:1.

What is claimed is:

1. A one pot process for preparing a 6-hydroxyl nal-opiate from a 6-keto nor-opiate, the process comprising:
   (a) contacting the 6-keto nor-opiate with an alkylating reagent to form a 6-keto nal-opiate, wherein the 6-keto nal-opiate is not isolated; and
   (b) contacting the 6-keto nal-opiate with a reducing agent and a proton acceptor to form the 6-hydroxyl nal-opiate;
   wherein the reducing agent is selected from the group consisting of a sulfinic acid reducing agent, a hydrosulphite, a borohydride reagent, an aluminum hydride reagent, and a catalytic hydrogen transfer reduction reagent;

wherein the catalytic hydrogen transfer reduction reagent comprises a transition metal and a hydrogen donor, the transition metal being selected from the group consisting of palladium and platinum; and wherein the process further comprises addition of a protic solvent after step (a).

2. The process of claim 1, wherein the alkylating reagent comprises an alkyl halide and the reducing agent is chosen from a hydrosulphite, a sulfinic acid reducing agent, a borohydride reagent, and a catalytic hydrogen transfer reduction regent.

3. The process of claim 1, wherein a 6-β-epimer of 6-hydroxyl nal-opiate is produced in a ratio of greater than 75:25 to a 6-α-epimer.

4. The process of claim 1, wherein a 6-α-epimer of 6-hydroxyl nal-opiate is produced in a ratio of greater than 75:25 to a 6-β-epimer.

5. A one pot process for producing a compound comprising Formula (I) from a compound comprising Formula (II), the process comprising:

(a) contacting the compound comprising Formula (II) with an alkylating reagent comprising $R^{17}$ to form an intermediate comprising Formula (III), wherein the intermediate comprising Formula Op is not isolated; and (b) contacting the intermediate comprising Formula (III) with a reducing agent and a proton acceptor to form the compound comprising Formula (I) according to the following reaction scheme:

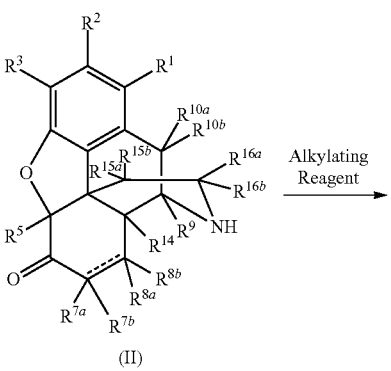

(II)

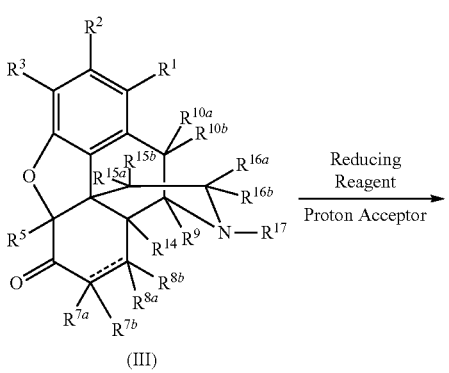

(III)

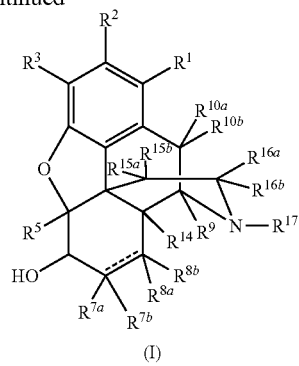

(I)

wherein, $R^1$, $R^2$, and $R^3$ are independently chosen from hydrogen, hydrocarbyl, substituted hydrocarbyl, halogen, hydroxyl, SH, $SR^{1811}$, $OR^{1811}$, and $NR^{1811}R^{1812}$;

$R^5$, $R^{7a}$, $R^{7b}$, $R^{8a}$, $R^{8b}$, $R^9$, $R^{10a}$, $R^{10b}$, $R^{14}$, $R^{15a}$, $R^{16a}$, and $R^{16b}$ are independently chosen from hydrogen, hydrocarbyl, substituted hydrocarbyl, halogen, hydroxyl, SH, $SR^{1811}$, $OR^{1811}$, and $NR^{1811}R^{1812}$, wherein any pair of $R^{\#a}$ and $R^{\#b}$ where # is chosen from 7, 8, 10, 15, and 16 may be optionally linked by groups chosen from =O, =S, and =NR$^{1813}$;

$R^{17}$ is chosen from hydrocarbyl or substituted hydrocarbyl;

$R^{1811}$, $R^{1812}$, and $R^{1813}$ are independently chosen from hydrogen, hydrocarbyl, and substituted hydrocarbyl;

the dashed lines between the C-7 and C-8 carbons represent a carbon-carbon double bond or a carbon-carbon single bond, provided that if there is a double bond between the C-7 and C-8 carbons then only one of $R^{7a}$ and $R^{7b}$ is present and only one of $R^{8a}$ or $R^{8b}$ is present; and provided that one or more of $R^1$, $R^2$, $R^3$, $R^5$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$ may be linked to form carbocyclic or heterocyclic rings;

wherein the reducing agent is selected from the group consisting of a sulfinic acid reducing agent, a hydrosulphite, a borohydride reagent, an aluminum hydride reagent, and a catalytic hydrogen transfer reduction reagent;

wherein the catalytic hydrogen transfer reduction reagent comprises a transition metal and a hydrogen donor, the transition metal being selected from the group consisting of palladium and platinum; and wherein the process further comprises addition of a protic solvent after step (a).

6. The process of claim 5, wherein the alkylating reagent comprises $R^{17}$ and a leaving group.

7. The process of claim 5, wherein the alkylating reagent comprises allyl bromide.

8. The process of claim 5, wherein $R^{17}$ is chosen from methyl, allyl, methanecyclopropyl, and methanecyclobutyl.

9. The process of claim 5, wherein $R^1$, $R^2$, $R^5$, $R^{7a}$, $R^{7b}$, $R^{8a}$, $R^{8b}$, $R^9$, $R^{10a}$, $R^{10b}$, $R^{15a}$, $R^{15b}$, $R^{16a}$, and $R^{16b}$ are hydrogen.

10. The process of claim 5, wherein $R^3$ and $R^{14}$ are chosen from hydrogen, hydroxyl and $OR^{1811}$.

11. The process of claim 5, wherein the reducing agent is chosen from a hydrosulphite, a sulfinic acid reducing agent, a borohydride reagent, and a catalytic hydrogen transfer reduction regent.

12. The process of claim 11, wherein the sulfinic acid reducing agent is chosen from formamidine sulfinic acid and hydroxymethane sulfinic acid.

13. The process of claim 11, wherein the reducing agent comprises sodium hydrosulphite.

14. The process of claim 5, wherein the C-5, C-6, C-9, C-13, and C-14 stereocenters of the compound comprising Formula (I) are chosen from RRRRR, RSRRR, RRRRS, RSRRS, RRRSR, RSRSR, RRSRR, RSSRR, SRRRR, SSRRR, RRRSS, RSRSS, RRSSR, RSSSR, SRSRR, SSSRR, SRRRS, SSRRS, SRRSR, SSRSR, RRSRS, RSSRS, RRSSS, RSSSS, SRRSS, SSRSS, SRSRS, SSSRS, SRSSR, SSSSR, SRSSS, and SSSSS, respectively, provided that the C-15 and the C-16 carbons are both either on the alpha face of the molecule or the beta face of the molecule.

15. The process of claim 5, wherein a 6-β-epimer of the compound comprising Formula (I) is produced in a ratio of greater than 75:25 to a 6-α-epimer.

16. The process of claim 5, wherein a 6-β-epimer of the compound comprising Formula (I) is produced in a ratio of greater than 95:5 to a 6-α-epimer.

17. The process of claim 5, wherein a 6-α-epimer of the compound comprising Formula (I) is produced in a ratio of greater than 75:25 to a 6-β-epimer.

18. The process of claim 5, wherein a 6-α-epimer of the compound comprising Formula (I) is produced in a ratio of greater than 95:5 to a 6-β-epimer.

19. The process of claim 5, wherein the compound comprising Formula (II) is contacted with the alkylating reagent in an organic solvent chosen from dimethylformamide, N-methylpyrrolidinone, dimethylacetamide, and mixtures thereof.

20. The process of claim 5, wherein the yield of the compound comprising Formula (I) is above 75%.

* * * * *